(12) United States Patent  
Emery et al.

(10) Patent No.: US 8,710,196 B2  
(45) Date of Patent: Apr. 29, 2014

(54) PROTEIN PURIFICATION

(75) Inventors: Jefferson C. Emery, Son Mateo, CA (US); Paul J. McDonald, San Francisco, CA (US); Rhona O'Leary, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/252,952

(22) Filed: Oct. 4, 2011

(65) Prior Publication Data

US 2012/0065381 A1 Mar. 15, 2012

Related U.S. Application Data

(62) Division of application No. 10/659,825, filed on Sep. 10, 2003, now Pat. No. 8,044,017.

(60) Provisional application No. 60/410,334, filed on Sep. 11, 2002.

(51) Int. Cl.  
*C07K 1/18* (2006.01)  
*C12P 21/08* (2006.01)

(52) U.S. Cl.  
USPC ...... 530/416; 530/412; 530/388.1; 530/289.1

(58) Field of Classification Search  
None  
See application file for complete search history.

(56) References Cited

U.S. PATENT DOCUMENTS 5,571,720 A * 11/1996 Grandics et al. ........... 435/286.1  
5,677,171 A 10/1997 Hudziak et al.  
6,339,142 B1 1/2002 Basey et al.  
6,417,355 B1 7/2002 Chapman et al.  
6,433,144 B1 8/2002 Morris et al.  
8,044,017 B2 * 10/2011 Emery et al. ................ 514/1.1  
2001/0034053 A1 * 10/2001 Winge ......................... 435/212

FOREIGN PATENT DOCUMENTS

WO WO 98/30694 7/1998  
WO WO 99/57134 * 11/1999 ............... C07K 1/18  
WO WO 00/02921 1/2000  
WO WO 00/55184 9/2000

OTHER PUBLICATIONS

Carter et al., "Humanization of an Anti-P185HER2 Antibody for Human Cancer Therapy" Proceedings of the National Academy of Sciences of USA, National Academy of Science, Washington, DC, US., 89(10):4285-4289 (1992), XP000275844, issn:0027-8424.  
Fukuoka, et al., "Studies of quality control of $^{99m}$Tc-labelled Macroaggregated Albumin—part 1. Aggregation of non-mercaptalbumin and its conformation", Nucl. Med. Biol., vol. 20, No. 5, pp. 643-648 (1993).  
Harris et al., "Identification of Multiple Sources of Charge Heterogeneity in a Recombinant Antibody" Journal of Chromatography B: Biomedical Sciences & Applications, Elsevier, Amsterdam, NL, 752(2): 233-245 (2001), XP004317158, ISSN: 1570-0233.  
Kawaguchi et al., "Rapid analysis of serum lactate dehydrogenase isoenzymes by high-performance ion-exchange chromatography", Journal of Chromatography, 378: 456-461 (1986).

* cited by examiner

*Primary Examiner* — Maury Audet  
(74) *Attorney, Agent, or Firm* — Diane Marschang; Ginger R. Dreger; Arnold & Porter LLP

(57) ABSTRACT

A method for purifying a polypeptide by ion exchange chromatography is described in which a gradient wash is used to resolve a polypeptide of interest from one or more contaminants.

14 Claims, 4 Drawing Sheets

LIGHT CHAIN

HEAVY CHAIN

```
1                                              15                              30                                 45
EVQLVESGGGLVQPGGSLRLSCAASG F N IKDTYIHWVRQAPGKGL 46                                             60                              75                                 90
EWVARIYPTNGYTRYADSVKGRFTIS A DTSKNTAYLQMNSLRAED 91                                             105                             120                                135
TAVYYCSRWGGDGFYAMDYWGQGTLVTVSSASTKGPSVFPLAPSS 136                                            150                             165                                180
KSTSGGTAALG CLVKDYFPEPVTVSWNSGALTSGVHTFPAVLQSS 181                                            195                             210                                225
GLYSLSSVVTVPS SSLGTQTYICNVNHKPSNTKVDKKVEPKSC DK 226                                            240                             255                                270
THTCPPCPAPELLGGPSVFLFPPKPKDT LMISRTPEVTCVV V D V S 271                                            285                             300                                315
HEDPEVKFNWYVDGVEVHNAKTKPREEQYNSTYRVVSVLTVLHQD 316                                            330                             345                                360
WLNGKEYKCKVSNKALPAPIEKTISKA K GQPREPQVYTL P P SRE E 361                                            375                             390                                405
MTKNQVSLTCLVKGFYPSDIAVEWESNGQPENNYKTTPPVL D SDG 406                                            420                             435                                449
SFFLYSKLTVDKSRWQQGNVFSCSVMHEALHNHYTQKSL S L S P G
```

FIGURE 1B

PROTEIN PURIFICATION

CROSS-REFERENCE TO RELATED APPLICATIONS

This application is a divisional of U.S. application Ser. No. 10/659,825, filed Sep. 10, 2003 (now U.S. Pat. No. 8,044, 017), which is a non-provisional application filed under 37 CFR 1.53(b)(1), claiming priority under 35 USC §119(c) to U.S. Provisional Application No. 60/410,334, filed Sep. 11, 2002, the entire contents of which are incorporated herein by reference.

BACKGROUND OF THE INVENTION

1. Field of the Invention

This invention relates generally to protein purification. In particular, the invention relates to a method for purifying a polypeptide (e.g. an antibody) from a composition comprising the polypeptide and at least one contaminant using the method of ion exchange chromatography.

2. Description of the Related Art

The large-scale, economic purification of proteins is an increasingly important problem for the biotechnology industry. Generally, proteins are produced by cell culture, using either eukaryotic or prokaryotic cell lines engineered to produce the protein of interest by insertion of a recombinant plasmid containing the gene for that protein. Since the cells typically used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through".

Ion exchange chromatography is a chromatographic technique that is commonly used for the purification of proteins. In ion exchange chromatography, charged patches on the surface of the solute are attracted by opposite charges attached to a chromatography matrix, provided the ionic strength of the surrounding buffer is low. Elution is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). In the past, these changes have been progressive; i.e., the pH or conductivity is increased or decreased in a single direction U.S. Pat. Nos. 6,339,142 and 6,417,355 (Basey et al.) describe ion exchange chromatography for purifying polypeptides.

U.S. Pat. Nos. 6,127,526 and 6,333,398 (Blank, G.) describe purifying proteins, such as anti-HER2 antibodies, by Protein A chromatography.

SUMMARY OF THE INVENTION

In one aspect, the present invention provides a method for purifying a polypeptide from a composition comprising the polypeptide and contaminants. The composition is loaded onto an ion exchange resin with an equilibrium buffer having a first salt concentration. The ion exchange resin is washed with a wash buffer until a predetermined protein concentration is measured in the flowthrough. During the wash the salt concentration of the wash buffer increases from an initial, second salt concentration that is greater than the salt concentration of the equilibration buffer, to a final, third salt concentration. A fixed volume of wash buffer at the final, third salt concentration is then passed over the resin. Finally, the polypeptide is eluted from the ion exchange resin exchange resin with elution buffer that has a salt concentration that is greater than the final salt concentration of the wash buffer.

In one embodiment the ion exchange resin is an anion exchange resin. In another embodiment the ion exchange resin is a cation exchange resin. Preferably, the cation exchange resin comprises sulphopropyl immobilized on agarose.

In another embodiment the elution buffer has a higher conductivity than the equilibration buffer. In a particular embodiment the elution buffer comprises about 145 mM Na/HOAc and the equilibration buffer comprises about 70 mM Na/HOAc. In another embodiment the elution buffer comprises about 100 mM NaCl and the equilibration buffer comprises about 45 mM NaCl.

The wash buffer preferably comprises a mixture of equilibration buffer and elution buffer. Thus, in one embodiment the increase in the salt concentration of the wash buffer during step (b) is achieved by increasing the proportion of elution buffer in the wash buffer. The proportion of elution buffer in the wash buffer may be increased at a constant rate. In one embodiment the increase in the proportion of elution buffer causes the salt concentration of the wash buffer to increase at a constant rate of from about 1 mM to about 3 mM per column volume of wash buffer.

In another embodiment the percentage of elution buffer in the wash buffer increases at two or more different rates during the course of washing in step (b). For example, the percentage of elution buffer in the wash buffer increases at a first rate for a first segment of the washing, at a second rate for a second segment of the washing and at a third rate for a third segment of the washing.

In one embodiment the polypeptide that is purified is an antibody. In this case, the contaminant may be a deamidated variant of the antibody. In a particular embodiment, the antibody binds HER2. In one embodiment the amount of antibody in the composition loaded onto the ion exchange resin is from about 15 mg to about 45 mg per mL of cation exchange resin.

In one embodiment the predetermined protein concentration corresponds to an OD of 0.6 measured at 280 nm. In another embodiment, from about 0.4 to about 1 column volumes of wash buffer are passed over the ion exchange resin in step (c). In a further embodiment the pH of the equilibration buffer, wash buffer and elution buffer is approximately the same, preferably approximately 5.5.

In another embodiment the method of purifying a polypeptide further comprises subjecting the composition comprising the polypeptide to one or more additional purification steps, so as to obtain a homogeneous preparation of the polypeptide. In a further embodiment, a pharmaceutical composition is prepared by combining the homogeneous preparation of the polypeptide with a pharmaceutically acceptable carrier. In another embodiment the purified polypeptide is conjugated with a heterologous molecule, for example polyethylene glycol, a label or a cytotoxic agent.

In another aspect, the invention provides a polypeptide which has been purified according to the method provided herein.

In a further aspect, the invention provides a method for purifying an antibody from a composition comprising the polypeptide and a contaminant. The antibody is bound to a cation exchange material with an equilibration buffer at a first conductivity. The cation exchange material is washed with a wash buffer, wherein the conductivity of the wash buffer increases from a second conductivity that is higher than the first conductivity to a third conductivity during the washing. A fixed volume of wash buffer at the third conductivity is then passed over the cation exchange material and the antibody is eluted from the cation exchange material with an elution buffer at a fourth conductivity that is higher than the third conductivity. The cation exchange resin preferably comprises sulphopropyl immobilized on agarose. In one embodiment the fixed volume of wash buffer passed over the cation exchange material is between about 0.4 column volumes and about 1.0 column volumes. The method may also include the step of washing the ion exchange material with a regeneration buffer following elution of the antibody.

In one embodiment the conductivity of the wash buffer increases at a constant rate from the second conductivity to the third conductivity, while in another embodiment the conductivity of the wash buffer increases at two or more different rates from the second conductivity to the third conductivity. In a particular embodiment the conductivity of the wash buffer increases at a first rate for a first segment of the washing, at a second rate for a second segment of the washing and at a third rate for a third segment of the washing.

Preferably the wash buffer comprises a mixture of equilibration buffer and elution buffer. In this case, the conductivity of the wash buffer may be increased by increasing the proportion of elution buffer in the wash buffer. In one embodiment the proportion of elution buffer in the wash buffer increases at a constant rate of about 6% during the first segment, at a constant rate of about 3.5% during the second segment and at a constant rate of about 2% during the third segment. In another embodiment the proportion of elution buffer in the wash buffer increases from about 26% to about 54% during the first segment, from about 54% to about 61% during the second segment and from about 61% to about 74% during the second segment.

In a further embodiment the cation exchange material is washed with about 5 column volumes of wash buffer in the first segment, about 2 column volumes of wash buffer in the second segment and about 6 column volumes of wash buffer in the third segment.

The conductivity of the wash buffer may be increased by increasing the percentage of elution buffer in the wash buffer. In another embodiment the conductivity of the wash buffer is increased by increasing the salt concentration therein.

In a further aspect, the invention provides a method for purifying an antibody from a composition comprising the antibody and a contaminant. Preferably the composition is loaded onto a cation exchange material, the cation exchange material is washed with a wash buffer with a conductivity that increases at a first rate from a first conductivity to a second conductivity, at a second rate from the second conductivity to a third conductivity and at a third rate from the third conductivity to a fourth conductivity, and the antibody is eluted from the ion exchange material. The amount of antibody in the composition loaded onto the cation exchange material is preferably from about 15 mg to about 45 mg of the antibody per ml of cation exchange material.

In a further aspect, the present invention provides a method for purifying a polypeptide from a composition comprising the polypeptide and a contaminant comprising loading the composition onto an ion exchange material, washing the cation exchange material with wash buffer using a multi-slope gradient until a predetermined protein concentration is measured in the flowthrough, and eluting the polypeptide from the ion exchange material.

In one embodiment the multi-slope gradient comprises two or more segments. Preferably, each segment of the multi-slope gradient has a shallower slope.

In another embodiment the method additionally comprises the step of washing the column with from 0.4 to 1 column volumes of wash buffer after the multi-slope gradient wash and prior to eluting the polypeptide. Preferably the wash buffer used in this additional step has the composition of the wash buffer at the end of the multi-slope gradient.

BRIEF DESCRIPTION OF THE DRAWINGS

Figure 1A:
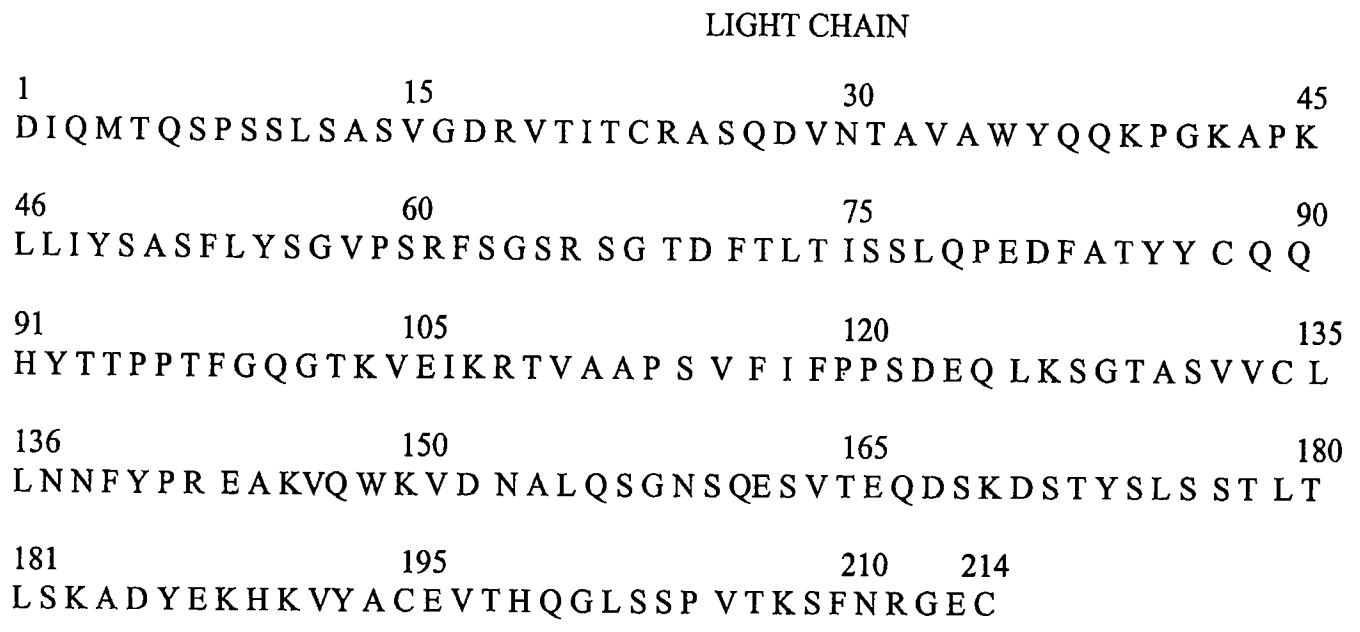

FIGS. 1A and 1B show the amino acid sequences of humMAb4D5-8 light chain (SEQ ID NO:1) and humMAb4D5-8 heavy chain (SEQ ID NO:2), respectively.

DETAILED DESCRIPTION OF THE PREFERRED EMBODIMENT

Definitions

Figure 2:
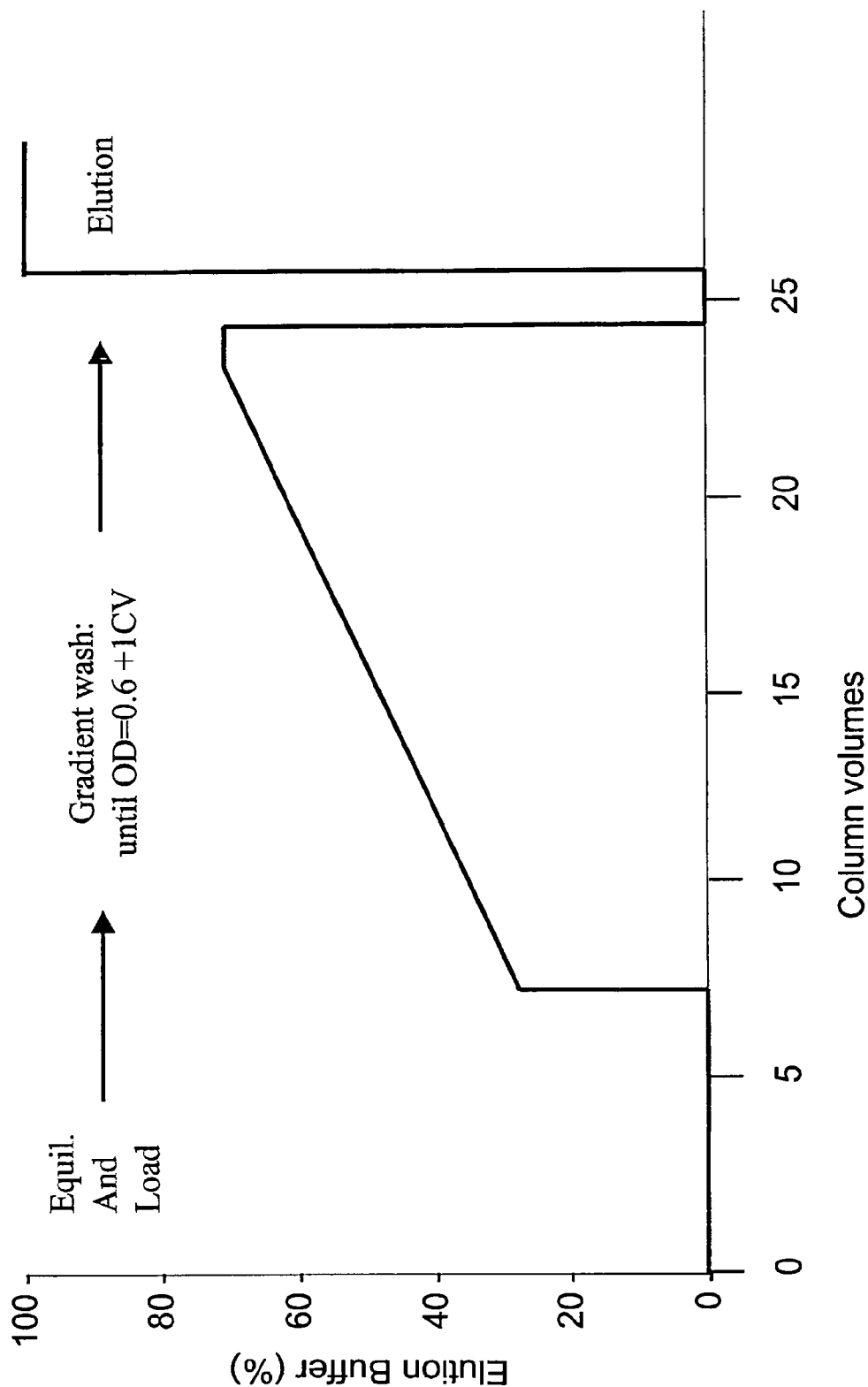
FIG. 2 is a graph illustrating a chromatography process with a linear gradient wash step. By testing gradients of various slopes (1-4 mM NaCl/CV), we found that although the yield and purity were more consistent at different loads than when a step wash procedure was used, there was still more variability than desired.

The "composition" to be purified herein comprises the polypeptide of interest and one or more contaminants. The composition may be "partially purified" (i.e. having been subjected to one or more purification steps, such as Protein A Chromatography) or may be obtained directly from a host cell or organism producing the polypeptide (e.g. the composition may comprise harvested cell culture fluid).

As used herein, "polypeptide" refers generally to peptides and proteins having more than about ten amino acids. Preferably, the polypeptide is a mammalian protein, examples of which include: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments and/or variants of any of the above-listed polypeptides. Most preferred is a full-length antibody that binds human HER2.

A "contaminant" is a material that is different from the desired polypeptide product. The contaminant may be, without limitation, a variant, fragment, aggregate or derivative of the desired polypeptide (e.g. a deamidated variant or an amino-aspartate variant), another polypeptide, nucleic acid, endotoxin, etc.

A "variant" or "amino acid sequence variant" of a starting polypeptide is a polypeptide that comprises an amino acid sequence different from that of the starting polypeptide. Generally, a variant will possess at least 80% sequence identity, preferably at least 90% sequence identity, more preferably at least 95% sequence identity, and most preferably at least 98% sequence identity with the native polypeptide. Percentage sequence identity is determined, for example, by the Fitch et al., *Proc. Natl. Acad. Sci. USA* 80:1382-1386 (1983), version of the algorithm described by Needleman et al., *J. Mol. Biol.* 48:443-453 (1970), after aligning the sequences to provide for maximum homology. Amino acid sequence variants of a polypeptide may be prepared by introducing appropriate nucleotide changes into DNA encoding the polypeptide, or by peptide synthesis. Such variants include, for example, deletions from, and/or insertions into and/or substitutions of, residues within the amino acid sequence of the polypeptide of interest. Any combination of deletion, insertion, and substitution is made to arrive at the final construct, provided that the final construct possesses the desired characteristics. The amino acid changes also may alter post-translational processing of the polypeptide, such as by changing the number or position of glycosylation sites. Other post-translational modifications include hydroxylation of proline and lysine, phosphorylation of hydroxyl groups of seryl, threonyl or tyrosyl residues, methylation of the α-amino groups of lysine, arginine and histidine side chains (T. E. Creighton, Proteins: Structure and Molecular Properties, W.H. Freeman & Co., San Francisco, pp. 79-86 (1983)). Methods for generating amino acid sequence variants of polypeptides are described in U.S. Pat. No. 5,534,615, expressly incorporated herein by reference, for example.

An "acidic variant" is a variant of a polypeptide of interest which is more acidic (e.g. as determined by cation exchange chromatography) than the polypeptide of interest. Acidic variants may be produced by the action of recombinant host cells on the expressed polypeptide. An example of an acidic variant is a deamidated variant. Glutaminyl and aspariginyl residues are frequently post-translationally deamidated to the corresponding glutamyl and aspartyl residues.

A "deamidated" variant of a polypeptide molecule is a polypeptide wherein one or more asparagine residue(s) of the original polypeptide have been converted to aspartate, i.e. the neutral amide side chain has been converted to a residue with an overall acidic character. For example, "deamidated human DNase" as used herein means human DNase that is deamidated at the asparagine residue that occurs at position 74 in the amino acid sequence of native mature human DNase (U.S. Pat. No. 5,279,823; expressly incorporated herein by reference). Deamidated huMAb4D5 antibody from the Examples below has Asn30 in CDR1 of either or both of the $V_L$ regions thereof converted to aspartate.

In preferred embodiments of the invention, the polypeptide is a recombinant polypeptide. A "recombinant polypeptide" is one which has been produced in a host cell which has been transformed or transfected with nucleic acid encoding the polypeptide, or produces the polypeptide as a result of homologous recombination. "Transformation" and "transfection" are used interchangeably to refer to the process of introducing nucleic acid into a cell. Following transformation or transfection, the nucleic acid may integrate into the host cell genome, or may exist as an extrachromosomal element. The "host cell" includes a cell in in vitro cell culture as well as a cell within a host animal. Methods for recombinant production of polypeptides are described in U.S. Pat. No. 5,534,615, expressly incorporated herein by reference, for example.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those polypeptides discussed above. Preferred molecular targets for antibodies encompassed by the present invention include CD polypeptides such as CD3, CD4, CD8, CD19, CD20 and CD34; members of the HER receptor family such as the EGF receptor, HER2, HER3 or HER4 receptor; cell adhesion molecules such as LFA-1, Mac1, p150, 95, VLA-4, ICAM-1, VCAM and av/b3 integrin including either a or b subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; polypeptide C etc. Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). In a further embodiment, "monoclonal antibodies" can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Polypeptides of Immunological Interest*, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework" or "FR" residues are those variable domain residues other than the hypervariable region residues as herein defined. The CDR and FR residues of the rhuMAb HER2 antibody of the example below (humAb4D5-8) are identified in Carter et al., *Proc. Natl. Acad. Sci. USA*, 89:4285 (1992).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)).

Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

"Antibody fragments" comprise a portion of a full length antibody, generally the antigen binding or variable region thereof. Examples of antibody fragments include Fab, Fab', $F(ab')_2$, and Fv fragments; diabodies; linear antibodies; single-chain antibody molecules; and multispecific antibodies formed from antibody fragments. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10:163-167 (1992)). In another embodiment, the $F(ab')_2$ is formed using the leucine zipper GCN4 to promote assembly of the $F(ab')_2$ molecule. According to another approach, $F(ab')_2$ fragments can be isolated directly from recombinant host cell culture. Other techniques for the production of antibody fragments will be apparent to the skilled practitioner.

In other embodiments, the antibody of choice is a single chain Fv fragment (scFv). See WO 93/16185. "Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The expression "linear antibodies" when used throughout this application refers to the antibodies described in Zapata et al. *Polypeptide Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

"Multispecific antibodies" have binding specificities for at least two different epitopes, where the epitopes are usually from different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. $F(ab')_2$ bispecific antibodies).

Methods for making bispecific antibodies are known in the art. Traditional production of full-length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

The phrase "ion exchange material" refers to a solid phase that is negatively charged (i.e. a cation exchange resin) or positively charged (i.e. an anion exchange resin). The charge may be provided by attaching one or more charged ligands to the solid phase, e.g. by covalent linking. Alternatively, or in addition, the charge may be an inherent property of the solid phase (e.g. as is the case for silica, which has an overall negative charge).

By "solid phase" is meant a non-aqueous matrix to which one or more charged ligands can adhere. The solid phase may be a purification column, a discontinuous phase of discrete particles, a membrane, or filter etc. Examples of materials for forming the solid phase include polysaccharides (such as agarose and cellulose) and other mechanically stable matrices such as silica (e.g. controlled pore glass), poly(styrenedivinyl)benzene, polyacrylamide, ceramic particles and derivatives of any of the above.

A "cation exchange resin" refers to a solid phase that is negatively charged and has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methyl-cellulose, BAKERBOND ABX™, sulphopropyl (SP) immobilized on agarose (e.g. SP-SEPHAROSE FAST FLOW™, SP-SEPHAROSE FAST FLOW XL™ or SP-SEPHAROSE HIGH PERFORMANCE™, from Pharmacia) and sulphonyl immobilized on agarose (e.g. S-SEPHAROSE FAST FLOW™ from Pharmacia).

The term "anion exchange resin" is used herein to refer to a solid phase which is positively charged, e.g. having one or more positively charged ligands, such as quaternary amino groups, attached thereto. Commercially available anion exchange resins include DEAE cellulose, QAE SEPHADEX™ and FAST Q SEPHAROSE™ (Pharmacia).

A "buffer" is a solution that resists changes in pH by the action of its acid-base conjugate components. Various buffers which can be employed depending, for example, on the desired pH of the buffer are described in *Buffers. A Guide for the Preparation and Use of Buffers in Biological Systems*, Gueffroy, D., Ed. Calbiochem Corporation (1975). In one embodiment, the buffer has a pH in the range from about 5 to about 7 (e.g. as in Example 1 below). Examples of buffers that will control the pH in this range include MES, MOPS, MOPSO, phosphate, acetate, citrate, succinate, and ammonium buffers, as well as combinations of these. The buffers used in the disclosed methods typically also comprise a salt, such as NaCL, KCl or NaHOAc.

"Equilibration buffer" is the buffer that is used to equilibrate the ion exchange resin. The equilibration buffer may also be used to load the composition comprising the polypeptide molecule of interest and one or more contaminants onto the ion exchange resin. The equilibration buffer preferably has a conductivity and/or pH such that the polypeptide molecule of interest is bound to the ion exchange resin.

The term "wash buffer" is used herein to refer to the buffer that is passed over the ion exchange resin following loading and prior to elution of the protein of interest. The wash buffer may serve to elute one or more contaminants from the ion exchange resin. The conductivity and/or pH of the wash buffer is/are such that the contaminants are eluted from the ion exchange resin, but not significant amounts of the polypeptide of interest. The "wash buffer" preferably comprises a mixture of equilibration buffer and elution buffer, and can thus be described by the percentage of elution buffer that it comprises in a given volume.

"Elution buffer" is used to elute the polypeptide of interest from the solid phase. The conductivity and/or pH of the elution buffer is/are such that the polypeptide of interest is eluted from the ion exchange resin.

A "regeneration buffer" may be used to regenerate the ion exchange resin such that it can be re-used. The regeneration buffer has a conductivity and/or pH as required to remove substantially all contaminants and the polypeptide of interest from the ion exchange resin.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is mmhos (mS/cm), and can be measured using a conductivity meter, such as those sold, e.g., by Orion. The conductivity of a solution may be altered by changing the concentration of ions therein. For example, the concentration of a buffering agent and/or the concentration of a salt (e.g. Na/HOAc, NaCl or KCl) in the solution may be altered in order to achieve the desired conductivity. Preferably, the salt concentration of the various buffers is modified to achieve the desired conductivity.

By "purifying" a polypeptide from a composition comprising the polypeptide and one or more contaminants is meant increasing the degree of purity of the polypeptide in the composition by removing (completely or partially) at least one contaminant from the composition. A "purification step" may be part of an overall purification process resulting in a "homogeneous" composition. "Homogeneous" is used herein to refer to a composition comprising at least about 70% by weight of the polypeptide of interest, based on total weight of the composition, preferably at least about 80% by weight, more preferably at least about 90% by weight, even more preferably at least about 95% by weight.

Unless indicated otherwise, the term "HER2" when used herein refers to human HER2 protein and "HER2" refers to human HER2 gene. The human HER2 gene and HER2 protein are described in Semba et al., *PNAS* (USA) 82:6497-6501 (1985) and Yamamoto et al. *Nature* 319:230-234 (1986) (Genebank accession number X03363), for example.

The term "huMAb4D5-8" when used herein refers to a humanized anti-HER2 antibody comprising the light chain amino acid sequence of SEQ ID NO:1 and the heavy chain amino acid sequence of SEQ ID NO:2 or amino acid sequence variants thereof which retain the ability to bind HER2 and inhibit growth of tumor cells which overexpress HER2 (see U.S. Pat. No. 5,677,171; expressly incorporated herein by reference).

The "pI" or "isoelectric point" of a polypeptide refers to the pH at which the polypeptide's positive charge balances its negative charge. pI can be calculated from the net charge of the amino acid residues of the polypeptide or can be determined by isoelectric focussing.

By "binding" a molecule to an ion exchange material is meant exposing the molecule to the ion exchange material under appropriate conditions (pH/conductivity) such that the molecule is reversibly immobilized in or on the ion exchange material by virtue of ionic interactions between the molecule and a charged group or charged groups of the ion exchange material.

By "washing" the ion exchange material is meant passing an appropriate buffer through or over the ion exchange material.

To "elute" a molecule (e.g. polypeptide or contaminant) from an ion exchange material is meant to remove the molecule therefrom by altering the ionic strength of the buffer surrounding the ion exchange material such that the buffer competes with the molecule for the charged sites on the ion exchange material.

"Treatment" refers to both therapeutic treatment and prophylactic or preventative measures. Those in need of treatment include those already with the disorder as well as those in which the disorder is to be prevented.

A "disorder" is any condition that would benefit from treatment with the polypeptide purified as described herein. This includes both chronic and acute disorders and diseases and those pathological conditions which predispose the mammal to the disorder in question.

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (TAXOL™, Bristol-Myers Squibb Oncology, Princeton, N.J.), and doxetaxel, toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors, such as tamoxifen and onapristone.

Modes For Carrying Out The Invention

The invention herein provides methods for purifying a polypeptide from a composition (e.g. an aqueous solution) comprising the polypeptide and one or more contaminants. The composition is generally one resulting from the recombinant production of the polypeptide, but may be that resulting from production of the polypeptide by peptide synthesis (or other synthetic means) or the polypeptide may be purified from a native source of the polypeptide. Preferably the polypeptide is an antibody, e.g. one which binds the HER2 antigen.

For recombinant production of the polypeptide, the nucleic acid encoding it is isolated and inserted into a replicable vector for further cloning (amplification of the DNA) or for expression. DNA encoding the polypeptide is readily isolated and sequenced using conventional procedures (e.g., where the polypeptide is an antibody by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g. as described in U.S. Pat. No. 5,534,615, specifically incorporated herein by reference).

Suitable host cells for cloning or expressing the DNA in the vectors herein are the prokaryote, yeast, or higher eukaryotic cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K lactis, K. fragilis* (ATCC 12,424), K bulgaricus (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated polypeptide are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines include, but are not limited to, monkey kidney CV1 cells transformed by SV40 (COS-7, ATCC CRL 1651); human embryonic kidney cells (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR(CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and human hepatoma cells (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

The host cells used to produce the polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the polypeptide can be produced intracellularly, in the periplasmic space, or directly secreted into the medium. If the polypeptide is produced intracellularly, as a first step, the particulate debris, either host cells or lysed cells (e.g. resulting from homogenization), is removed, for example, by centrifugation or ultrafiltration. Where the polypeptide is secreted into the medium, supernatants from such expression systems are generally first concentrated using a commercially available protein concentration filter, for example, an Amicon or Millipore Pellicon ultrafiltration unit.

The polypeptide is then subjected to one or more purification steps, including the ion exchange chromatography method as described herein. Examples of additional purification procedures which may be performed prior to, during, or following the ion exchange chromatography method include fractionation on a hydrophobic interaction chromatography (e.g. on phenyl sepharose), ethanol precipitation, isoelectric focusing, Reverse Phase HPLC, chromatography on silica, chromatography on HEPARIN SEPHAROSE™, further anion exchange chromatography and/or further cation exchange chromatography, chromatofocusing, SDS-PAGE, ammonium sulfate precipitation, hydroxylapatite chromatography, gel electrophoresis, dialysis, and affinity chromatography (e.g. using protein A, protein G, an antibody, a specific substrate, ligand or antigen as the capture reagent).

Ion exchange chromatography is performed as described herein. A decision is first made as to whether an anion or cation exchange resin is to be employed. In general, a cation exchange resin may be used for polypeptides with pI's greater than about 7 and an anion exchange resin may be used for polypeptides with pI's less than about 7.

The anion or cation exchange resin is prepared according to known methods, following the manufacturer's instructions. Usually, an equilibration buffer is passed through the ion exchange resin prior to loading the composition comprising the polypeptide of interest and one or more contaminants onto the resin. Conveniently, the equilibration buffer is the same as the loading buffer, but this is not required. The composition of the various buffers used for the chromatography may depend in part on whether a cation or anion exchange resin is employed.

Following equilibration, an aqueous solution comprising the polypeptide of interest and contaminant(s) is loaded onto the cation exchange resin using a buffer that is at a pH and/or conductivity such that the polypeptide and the contaminant bind to the cation exchange resin. As discussed above, the equilibration buffer may be used for loading. In a preferred embodiment, the equilibration buffer is at a first low conductivity (e.g. from about 4 to about 5 mmhos) during loading. An exemplary pH for the equilibration buffer is about 5.5.

The amount of the polypeptide of interest loaded onto the resin may depend on a variety of factors, including, for example, the capacity of the resin, the desired yield, and the desired purity. Preferably, from about 1 mg of protein/ml of resin to about 100 mg of protein/ml of resin, more preferably from about 10 mg/ml to about 75 mg/ml and even more preferably from about 15 mg/ml to about 45 mg/ml of the polypeptide (e.g. of a full-length antibody) is loaded on the ion exchange resin.

After loading, the cation exchange resin is washed. During the wash process, wash buffer is passed over the resin. The composition of the wash buffer is typically chosen to elute as many contaminants as possible from the resin without eluting a substantial amount of the polypeptide of interest. This may be achieved by using a wash buffer with an increased conductivity or pH, or both, compared to the equilibration buffer. The composition of the was buffer may be constant or variable over the wash process, as described below.

In one embodiment, the wash buffer comprises equilibration buffer in which the salt concentration has been increased. The salt concentration may be increased by any method known in the art. In the preferred embodiment the wash buffer is a mixture of equilibration buffer and elution buffer. In this case, the desired salt concentration in the wash buffer is achieved by increasing the percentage of the higher salt buffer in the wash buffer. The elution buffer typically has a higher salt concentration and conductivity than the equilibration buffer. For example, in the preferred embodiment the elution buffer preferably has a conductivity of between about 8 mS/cm and about 10 mS/cm, more preferably between about 8.5 mS/cm and 9.5 mS/cm, while the equilibration buffer has a conductivity of between about 4 and 6 mS/cm, more preferably between about 4.5 and 5.5 mS/cm. Thus, as the percentage of elution buffer is increased, the salt concentration and the conductivity of the wash buffer increase.

The increase in salt concentration from the equilibration buffer to the initial wash buffer may be step-wise or gradual as desired. The amount of the initial increase will depend upon the desired conductivity of the wash buffer at the start of the wash process.

Preferably, the initial increase in the salt concentration is achieved by a stepwise increase in the percentage of elution buffer in the wash buffer. One of skill in the art will be able to determine the amount of the increase in elution buffer based on the salt concentration of the equilibration buffer, the salt concentration of the elution buffer and the desired conductivity. The increase is preferably from about 0% elution buffer to an initial percentage of between about 10% and 50% elution buffer, more preferably to between about 20% and 30% elution buffer and still more preferably to about 25% elution buffer. In the preferred embodiment, the initial increase is to an initial percentage of about 26% elution buffer.

A wash buffer with a fixed salt concentration may be used for the entire wash. In this case the composition of the wash buffer will not vary significantly from the initial composition for the duration of the wash. Preferably, however, a gradient wash is used, in which the composition of the wash buffer changes over the course of the wash process.

In one embodiment a linear salt concentration gradient wash is used. In this wash process, the salt concentration of the wash buffer changes at a constant rate, generally increasing from a first initial concentration to a higher second concentration, as the wash progresses. A linear salt concentration gradient is preferably created by increasing the percentage of elution buffer in the wash buffer at a constant rate. The rate of increase in the salt concentration of the wash buffer may be described by the slope of the line formed by plotting the percentage of elution buffer in the wash buffer against column volumes of wash buffer that have passed over the column.

An exemplary linear gradient wash is depicted in FIG. 2. In this case, a single slope defines the linear salt concentration gradient and thus the rate of change in the salt concentration during the wash. The rate of change, and thus the slope, is chosen to achieve the greatest yield of the polypeptide of interest with the highest purity. One of skill in the art will be able to determine the optimum slope for a particular polypeptide and load mass. In general, loads with a higher protein concentration will require a steeper slope, while smaller loads require a shallower slope to achieve the desired yield and purity for a given protein.

Figure 3:
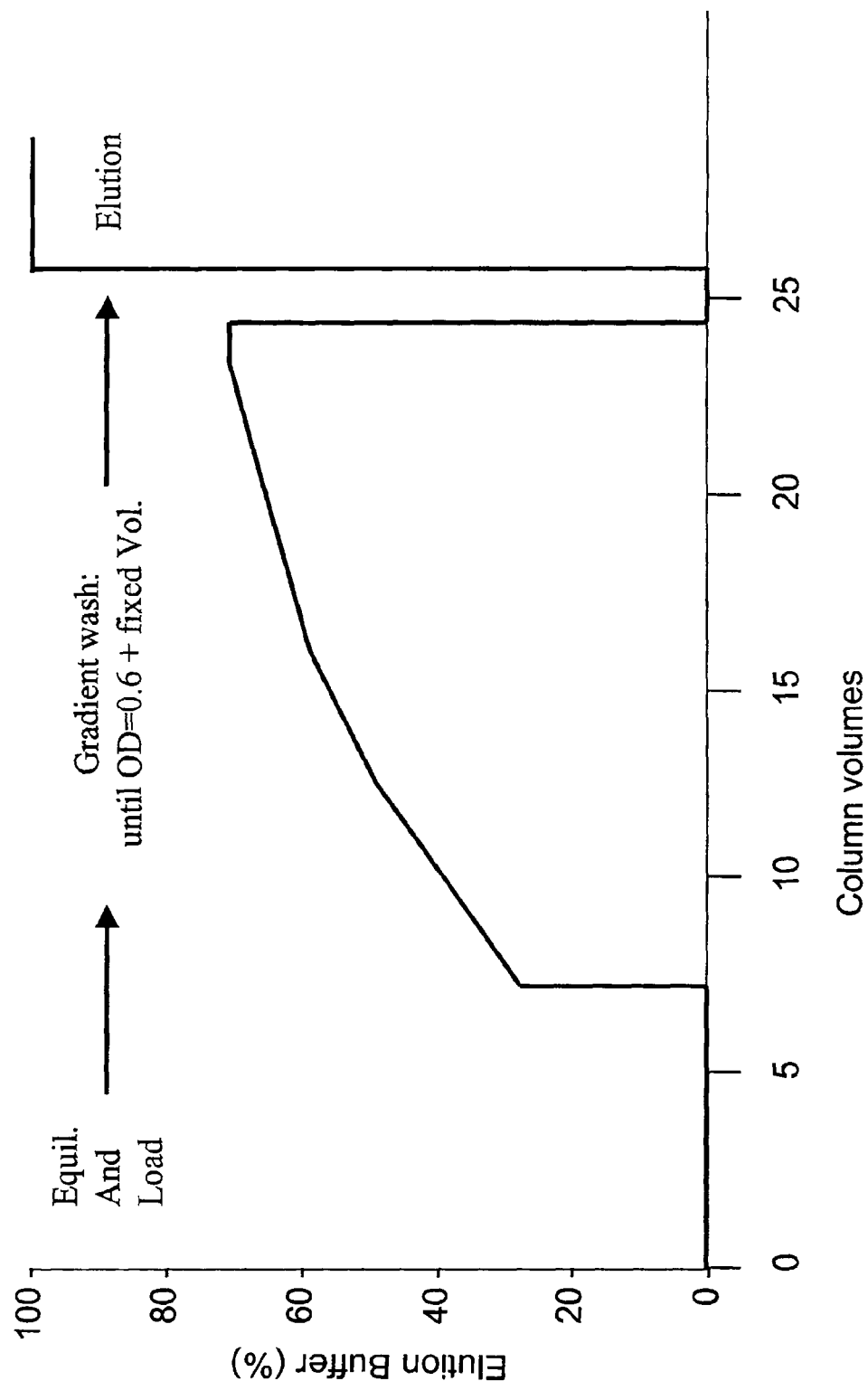
FIG. 3 is a graph illustrating a chromatography process with a multi-slope gradient wash. By using a linear gradient with three segments (having progressively shallower slopes), consistent yield and purity can be achieved across the entire load range. In addition, as shown below, the trade off between yield and purity can be fine tuned by adjusting the end-wash delay volume after OD of 0.6 is achieved.

In another embodiment, a multi-slope gradient wash is used. In this wash process, a number of linear salt gradients with different slopes are carried out consecutively. Thus, the salt concentration in the wash buffer passing over the column increases at a first rate for a first portion of the wash, or segment, and at one or more additional rates for other defined portions, or segments of the wash. A three segment salt gradient is illustrated in FIG. 3 and described in more detail below.

Each linear salt gradient segment accounts for a fraction of the total wash volume that passes over the resin. The proportion of the total wash volume accounted for by each particular gradient segment will vary depending on the number and duration of the segments.

One of skill in the art will recognize that the number of segments is not limited in any way and will be chosen based on the particular circumstances. Factors that will affect the preferred number of segments include, for example, the nature of the protein being eluted, the total wash volume and the anticipated load range. For example, a multi-slope gradient wash allows a single wash protocol to be effective across a wide column load range. Thus, if a variety of different load masses will be purified using the same wash protocol, multiple segments will result in more consistent yield and purity across the load range.

Each segment of a multi-segment wash preferably ends when a predetermined condition is met. For example when the concentration of protein in the flow through reaches a predetermined level, or when the wash buffer has reached a desired conductivity. In the preferred embodiment, each segment ends when the wash buffer comprises a predetermined percentage of elution buffer, and thus has a desired conductivity.

In addition, if the wash comprises more than one segment, the slope is preferably greater in the first segment than in any additional segments. As a result, the increase in the conductivity of the wash buffer will be greater in the first segment than in subsequent segments. If the salt concentration is varied by increasing the percentage of elution buffer in the wash buffer, the increase in the percentage of elution buffer per column volume will be greater in the first segment than in subsequent segments.

The gradient wash preferably ends when a predetermined amount of protein is detected in the flow through. In the preferred embodiment, the gradient wash ends when the protein concentration in the flow through reaches a level corresponding to an optical density measurement of 0.6 at 280 nm.

The wash process is optionally completed by passing a fixed amount of wash buffer over the column. This is referred to as the "end-wash delay volume." Following the last linear gradient segment, a fixed volume of the wash buffer with the highest conductivity from the gradient wash is passed over the column. Using a larger end-wash delay volume increases the purity of the eluted protein but may lead to a somewhat decreased yield. Conversely, decreasing the fixed volume leads to an increased yield, but may produce a slight decrease in the purity of the recovered protein. Thus, the fixed volume may be chosen by the skilled artisan to achieve the desired yield and purity. Preferably the end-wash delay volume is from 0 to 2 column volumes of the final wash buffer, more preferably from 0.2 to 1 column volume.

In a preferred embodiment, a multi-slope gradient wash with three segments is used. This embodiment is illustrated in FIG. 3. The first segment preferably accounts for about a third of the total wash volume, during which the percentage of elution buffer in the wash buffer increases from an initial percentage of about 26% to about 50%, more preferably about 54%, resulting in a corresponding increase in the salt concentration and conductivity. About 5 column volumes of wash buffer are passed over the column during this first linear gradient segment. This represents a change of between about 5% and 6% elution buffer per column volume, as can be seen in the slope of the first segment in FIG. 3.

A second linear gradient segment is begun by modifying the rate of change of the percentage of elution buffer in the wash buffer. In the preferred embodiment the rate of change of the percentage of elution buffer is reduced to about 3.5% per column volume. The second segment preferably continues for approximately one sixth of the total wash volume. Thus, about 2 column volumes are passed over the column during the second segment. Preferably the second segment ends when the percentage of elution buffer has increased to about 60%, more preferably about 61%.

In the third segment, the rate of increase of elution buffer is further reduced, preferably to about 2% per column volume, more preferably to about 2.13% per column volume. The third segment is the longest of the three and accounts for about half of the total wash volume, with about 6 column volumes of wash buffer passing over the column. The third segment ends when an OD of 0.6 is measured in the flow through. Over the entire gradient wash, the percentage of elution buffer will have increased to about 75%, more preferably about 74% when an OD of 0.6 is achieved.

Following the wash process, a predetermined amount of equilibration buffer is optionally passed over the column. Preferably from 0 to 2 column volumes of equilibration buffer are passed over the column. More preferably 1 column volume of equilibration buffer is passed over the column.

The desired polypeptide molecule is subsequently eluted from the ion exchange resin. This is achieved using an elution buffer that has a pH and/or conductivity such that the desired polypeptide no longer binds to the ion exchange resin and therefore is eluted therefrom. In the preferred embodiment, the conductivity of the elution buffer exceeds that of the equilibration buffer. Alternatively, or in addition, the pH of the elution buffer may be increased relative to the equilibration buffer (for example, the pH of the elution buffer may about 6.0). The change in conductivity and/or pH from the wash buffer to the elution buffer may be step-wise or gradual, as desired. As discussed above, the elution buffer preferably has a conductivity of between about 8 mS/cm and about 10 mS/cm, more preferably between about 8.5 mS/cm and 9.5 mS/cm. Hence, the desired polypeptide is retrieved from the cation exchange resin at this stage in the method.

The changes in conductivity are generally as described above with respect to both a cation exchange resin and an anion exchange resin. One of skill in the art will be able to optimize the methods for either type of resin.

In the preferred embodiment of the invention, a single parameter (i.e. either conductivity or pH) is changed to achieve elution of both the polypeptide and contaminant, while the other parameter (i.e. pH or conductivity, respectively) remains about constant. For example, while the conductivity of the various buffers may differ, the pH's thereof may be essentially the same.

In an optional embodiment of the invention, the ion exchange resin is regenerated with a regeneration buffer after elution of the polypeptide, such that the column can be re-used. Generally, the conductivity and/or pH of the regeneration buffer is/are such that substantially all contaminants and the polypeptide of interest are eluted from the ion exchange resin. Generally, the regeneration buffer has a very high conductivity for eluting contaminants and polypeptide from the ion exchange resin.

The method herein is particularly useful for resolving a polypeptide molecule of interest from at least one contaminant, where the contaminant and polypeptide molecule of interest differ only slightly in ionic charge. The method may also be used, for example, to resolve a polypeptide from a glycosylation variant thereof, e.g. for resolving a variant of a polypeptide having a different distribution of sialic acid compared to the non-variant polypeptide.

The polypeptide preparation obtained according to the ion exchange chromatography method herein may be subjected to additional purification steps, if necessary. Exemplary further purification steps have been discussed above.

Optionally, the polypeptide is conjugated to one or more heterologous molecules as desired. The heterologous molecule may, for example, be one which increases the serum half-life of the polypeptide (e.g. polyethylene glycol, PEG), or it may be a label (e.g. an enzyme, fluorescent label and/or radionuclide) or a cytotoxic molecule (e.g. a toxin, chemotherapeutic drug, or radioactive isotope etc).

A therapeutic formulation comprising the polypeptide, optionally conjugated with a heterologous molecule, may be prepared by mixing the polypeptide having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. "Pharmaceutically acceptable" carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The humMAb4D5-8 antibody of particular interest herein may be prepared as a lyophilized formulation, e.g. as described in WO 97/04801; expressly incorporated herein by reference.

The formulation herein may also contain more than one active compound as necessary for the particular indication being treated, preferably those with complementary activities that do not adversely affect each other. Such molecules are suitably present in combination in amounts that are effective for the purpose intended. For example, for an anti-HER2 antibody a chemotherapeutic agent, such as a taxoid or tamoxifen, may be added to the formulation.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulation to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the polypeptide variant, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The polypeptide purified as disclosed herein or the composition comprising the polypeptide and a pharmaceutically acceptable carrier is then used for various diagnostic, therapeutic or other uses known for such polypeptides and compositions. For example, the polypeptide may be used to treat a disorder in a mammal by administering a therapeutically effective amount of the polypeptide to the mammal.

The following examples are offered by way of illustration and not by way of limitation. The disclosures of all citations in the specification are expressly incorporated herein by reference.

EXAMPLES

Full length human IgG rhuMAb HER2 (humAb4D5-8 in Carter et al. *Proc. Natl. Acad. Sci.* 89: 4285-4289 (1992) comprising the light chain amino acid sequence of SEQ ID NO:1 and heavy chain amino acid sequence of SEQ ID NO:2) was produced recombinantly in CHO cells. Following protein production and secretion to the cell culture medium, the CHO cells were separated from the cell culture medium by tangential flow filtration (PROSTACK™). Protein A chromatography was then performed by applying the Harvested Cell Culture Fluid (HCCF) from the CHO cells directly to an equilibrated PROSEP A™ column (Bioprocessing, Ltd).

Following Protein A chromatography, cation exchange chromatography was performed using a sulphopropyl (SP-SEPHAROSE FAST FLOW XL™ (SPXLFF) column (Pharmacia) to further separate the desired anti-HER2 antibody molecule. An SPXLFF™ column was packed. The dimensions were: 100 cm diameter and 35 cm bed height. The conductivity of the pool was reduced by the addition of an equal volume of sterile water for injection (SWFI).

The chromatography runs for these studies were performed with Pharmacia's UNICORN™ FPLC system. A number of chromatography runs were performed with load densities of 15, 30, and 45 mg of rhuMAb HER2 per mL of SPXLFF resin. In addition, the delay volume following the gradient wash was varied. Delay volumes of 1.0, 0.8, 0.6 and 0.4 column volumes following the gradient were tested.

The protein concentration of each chromatography fraction was determined by spectrophometric scans of each sample. The results were used to calculate product recovery yields. The extinction coefficient for rhuMAb HER2 is 1.45. Calculations used to derive the results are:

$$\text{Protein Concentration(mg/mL)} = \frac{280 \text{ nm}}{1.45} \times \text{Dilution Factor}$$

Protein Mass(mg) in Each Fraction =

Protein Concentration(mg/mL) × Fraction Volume (mL)

$$\text{Yield(\%)} = \frac{\text{Fraction Mass(mg)}}{\text{Total Mass(mg)}} \times 100$$

Deamidated and other acidic variants of rhuMAb HER2 were produced when the antibody was made by recombinant DNA technology. Fractions from each of the study chromatographies were tested for the relative amount of variant antibody by Dionex HPIEC chromatography. The deamidated and other acidic variants constituted from about 15 to about 20% of the composition obtained from the initial Protein A chromatography. It was discovered that the ion exchange methods described below could be used to substantially reduce the amount of deamidated and other acidic variants in the anti-HER2 composition, typically by about 50% or more.

Example 1

The SPXLFF column was prepared for load by sequential washes with regeneration buffer (0.5 N NaOH) followed by equilibration buffer (30 mM MES/45 mM NaCl, pH 5.6). The column was then loaded with Protein A pool adjusted to a pH of 5.60±0.05 and a conductivity of 5.8±0.2 mmhos. The column was washed using a linear salt gradient, essentially as depicted in FIG. 2. Prior to beginning the linear gradient, elution buffer (30 mM MES, 100 mM NaCl, pH 5.6) was mixed with equilibration buffer to produce an initial wash buffer that comprised about 26% elution buffer. The slope of the linear gradient was varied in different experiments, with rates of increase of salt concentration of 1 mM NaCl/Column volume (CV), 2 mM/CV and 3 mM/CV used. The linear gradient continued until an OD of 0.6 at 280 nm was measured in the flow through. The column was then washed with 1 CV of the ultimate wash buffer.

rhuMAb HER2 was then eluted from the column with elution buffer (30 mM MES/100 mM NaCl, pH 5.6). Following elution, the column was regenerated with regeneration buffer (0.5 N NaOH).

As can be seen in Table 1, the step yield varied as a result of slope and load mass.

TABLE 1

Step Yield as a Function of Gradient Slope and Load Mass

| Slope | 15 mg/ml | 30 mg/ml | 45 mg/ml |
|---|---|---|---|
| 1 mM/CV | 83% | 85% | 90% |
| 2 mM/CV | 81% | 81% | 84% |
| 3 mM/CV | 69% | 73% | 77% |

The purity was measured in terms of acidic variants by Dionex HPIEC. As can be seen in Table 2, the purity generally increased with increasing gradient slope. The load comprised 17% acid variants in all cases.

TABLE 2

Dionex HPIEC Purity Results; % Acidic Variants

| Slope | 15 mg/ml | 30 mg/ml | 45 mg/ml |
|---|---|---|---|
| 1 mM/CV | 7% | 12% | 14% |
| 2 mM/CV | 4% | 7% | 10% |
| 3 mM/CV | 2% | 4% | 7% |

Example 2

An SPXLFF column, as described above, was prepared for load by sequential washes with regeneration buffer (0.5 N NaOH) followed by equilibration buffer (30 mM MES/70 mM Na/HOAc, pH 5.5). The column was then loaded with Protein A pool adjusted to a pH of 5.60±0.05 and a conductivity of 5.8±0.2 mmhos.

Following loading, the column was washed using a multi-slope salt gradient with three distinct segments, each having a progressively shallower slope, essentially as illustrated in FIG. 3. The gradient parameters are shown in Table 3 below.

The wash began with an initial stepwise increase in the salt concentration of the equilibration buffer to form the initial wash buffer. The initial wash buffer was created by mixing elution buffer (30 mM MES, 145 mM Na/HOAc, pH 5.5) with equilibration buffer to produce a buffer that comprised 26% elution buffer. During the first linear gradient segment the column was washed with approximately 4.9 column volumes of wash buffer, during which the percentage of elution buffer in the wash buffer increased at a rate of about 5.71% per column volume. Thus, at the end of the first linear gradient segment, the wash buffer comprised 54% elution buffer.

During the second linear gradient segment 2.0 column volumes of wash buffer were passed over the column. During this segment the percentage of elution buffer increased at a rate of 3.5%. Thus, at the end of the second segment the wash buffer comprised 61% elution buffer.

Finally, during the third linear gradient segment 6.1 column volumes of wash buffer were passed over the column, with the percentage of elution buffer in the wash buffer increasing at a rate of 2.13% per column volume. The third linear gradient segment ended when an OD of 0.6 at 280 nm was measured in the flow through. At this point the wash buffer comprised 74% elution buffer.

Following the third linear gradient segment a fixed volume of the final wash buffer (i.e. 74% elution buffer) was passed over the column. Fixed volumes of 0.8, 0.6 and 0.4 column volumes were used in different experiments.

rhuMAb HER2 was then eluted from the column with elution buffer (30 mM MES/145 mM Na/HOAc, pH 5.5). Following elution, the column was regenerated with regeneration buffer (0.5 N NaOH).

TABLE 3

Gradient Parameters

|  | % elution buffer (end of segment) | Total Wash Volume at End of Segment (Column Volumes) | Total Segment Volume (CV) | Slope % elution buffer/CV |
|---|---|---|---|---|
| Gradient Start | 26% | 0 | 0 |  |
| Segment 1 | 54% | 4.9 | 4.9 | 5.71% |
| Segment 2 | 61% | 6.9 | 2.0 | 3.50% |
| Segment 3 | 74% | 13 | 6.1 | 2.13% |

The effect of rhuMAb HER2 load and end-wash delay volume on product recovery, and product quality was evaluated. The results presented in Tables 4 and 5 show that it is possible to achieve consistent yield and acidic variant removal over a wide load range by using a multi-slope gradient wash. In addition, the results demonstrate that the trade off between yield and purity can be fine tuned as desired by adjusting the end-wash delay volume after an OD of 0.6 is achieved.

As can be seen in Table 4, for a given end-wash delay volume, the step yield does not vary significantly. A larger end-wash delay volume decreases the yield somewhat at all load masses. However, as shown in Table 5, increasing the end-wash delay volume increases the purity of the eluted protein. Thus, one of skill in the art will be able to select an end-wash delay volume that achieves the desired yield and purity.

TABLE 4

Step Yield as a Function of Wash Delay Volume and Load Mass

|  | 15 mg/ml | 30 mg/ml | 45 mg/ml |
|---|---|---|---|
| 0.8 CV | 79% | 80% | 81% |
| 0.6 CV | 80% | 81% | 83% |
| 0.4 CV | 83% | 84% | 85% |

TABLE 5

Dionex HPIEC Purity; % Acidic Variants

|  | 15 mg/ml | 30 mg/ml | 45 mg/ml |
|---|---|---|---|
| 0.8 CV | 6% | 7% | 9% |
| 0.6 CV | 8% | 10% | 11% |
| 0.4 CV | 10% | 11% | 12% |

Based on load of 19% acidic variants.

By using a multi-slope gradient with three segments, each having a progressively shallower slope, consistent yield and purity can be achieved across a wide load range. Between the ranges of 15 to 45 mg of antibody per mL of resin, there is little variation in the yield or the quality of rhuMAb HER2 recovered in the elution pool for a given column wash delay volume.

What is claimed is:

1. A method for purifying an antibody from a composition comprising the antibody and a contaminant, which method comprises the following steps performed sequentially:
   (a) binding the antibody to a cation exchange material with an equilibration buffer at a first conductivity;
   (b) washing the cation exchange material with a wash buffer, wherein the conductivity of the wash buffer increases from a second conductivity that is higher than the first conductivity to a third conductivity during the washing;
   (c) passing a fixed volume of wash buffer at the third conductivity over the cation exchange material; and
   (d) eluting the antibody from the cation exchange material with an elution buffer at a fourth conductivity that is higher than the third conductivity.

2. The method of claim 1 wherein the cation exchange resin comprises sulphopropyl immobilized on agarose.

3. The method of claim 1 wherein the conductivity of the wash buffer increases at a constant rate from the second conductivity to the third conductivity.

4. The method of claim 1 wherein the conductivity of the wash buffer increases at two or more different rates from the second conductivity to the third conductivity.

5. The method of claim 4 wherein the conductivity of the wash buffer increases at a first rate for a first segment of the washing, at a second rate for a second segment of the washing and at a third rate for a third segment of the washing.

6. The method of claim 5 wherein the wash buffer comprises a mixture of equilibration buffer and elution buffer.

7. The method of claim 6 wherein the conductivity of the wash buffer is increased by increasing the proportion of elution buffer in the wash buffer.

8. The method of claim 7 wherein the proportion of elution buffer in the wash buffer increases at a constant rate of about 6% during the first segment, at a constant rate of about 3.5% during the second segment and at a constant rate of about 2% during the third segment.

9. The method of claim 7 wherein the proportion of elution buffer in the wash buffer increases from about 26% to about 54% during the first segment, from about 54% to about 61% during the second segment and from about 61% to about 74% during the second segment.

10. The method of claim 5 wherein the cation exchange material is washed with about 5 column volumes of wash buffer in the first segment, about 2 column volumes of wash buffer in the second segment and about 6 column volumes of wash buffer in the third segment.

11. The method of claim 1 wherein the conductivity of the wash buffer is increased by increasing the proportion of elution buffer in the wash buffer.

12. The method of claim 1 wherein the conductivity of the wash buffer is increased by increasing the salt concentration therein.

13. The method of claim 1 wherein the fixed volume of wash buffer passed over the cation exchange material in step (c) is between about 0.4 column volumes and about 1.0 column volumes.

14. The method of claim 1 further comprising washing the ion exchange material with a regeneration buffer after step (d).

* * * * *

SEQUENCE LISTING

<160> NUMBER OF SEQ ID NOS: 2

<210> SEQ ID NO 1
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 1

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 2
<211> LENGTH: 449
<212> TYPE: PRT
<213> ORGANISM: Artificial Sequence
<220> FEATURE:
<223> OTHER INFORMATION: Synthetic Polypeptide

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

-continued

```
Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315                     320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Glu Glu Met Thr Lys Asn Gln Val Ser Leu
        355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly
```